(12) United States Patent
Buettner

(10) Patent No.: US 7,422,845 B2
(45) Date of Patent: Sep. 9, 2008

(54) DETECTION OF NO BY USING GUANYLYL CYCLASE AND CGMP PRODUCTION AS A READOUT SYSTEM

(75) Inventor: Frank Buettner, Attenweiler (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 281 days.

(21) Appl. No.: 10/993,053

(22) Filed: Nov. 19, 2004

(65) Prior Publication Data

US 2005/0112717 A1 May 26, 2005

Related U.S. Application Data

(60) Provisional application No. 60/529,203, filed on Dec. 12, 2003.

(30) Foreign Application Priority Data

Nov. 26, 2003 (EP) .................................. 03027159

(51) Int. Cl.
*C12Q 1/00* (2006.01)
(52) U.S. Cl. ............................................ 435/4; 435/21
(58) Field of Classification Search .................. 435/4, 435/21
See application file for complete search history.

(56) References Cited

U.S. PATENT DOCUMENTS 5,695,761 A * 12/1997 Denhardt et al. ......... 424/184.1
2004/0002129 A1 1/2004 Hennies et al.

FOREIGN PATENT DOCUMENTS

WO WO 02/20831 3/2002

OTHER PUBLICATIONS

Mayer B. et al. A New Pathway of Nitric Oxide/Cyclic GMP Signaling Involving S-Nitrosoglutathione. J of Biological Chemistry 273(6)3264-70, Feb. 6, 1996.*
Miller L. et al. A-350619: A Novel Activator of Soluble Guanylyl Cyclase. Life Sciences 72 1015-1025, Jan. 17, 2003.*
Ignarro L. Physiology and Pathophysiology of Nitric Oxide. Kidney Int 49(Supp55)S2-S5, 1996.*
Bernd Mayer, et al. "A New Pathway of Nitric Oxide/Cyclic GMP Signaling Involving S-Nitrosoglutathione", J. Biol. Chem. vol. 273, No. 6, pp. 3264-3270, 1996.
International Search Report for PCT/EP2004/013707 mailed on Apr. 19, 2005.
Bernd Mayer et al; Biosynthesis and Action of Nitric Oxide in Mammalian Cells; Trends Biochemical Science (1997) vol. 22, pp. 477-481.
Patrick Vallace et al; Blocking NO Synthesis: How, Where and Why?; Nature Reviews/Drug Discovery (2002) vol. 1 pp. 939-950.
Wendy K. Alderton et al; Nitric Oxide Synthases: Structure, Function and Inhibition; Biochemical Journal (2001) vol. 357 pp. 593-615.

Stefan P. Janssens et al; Cloning and Expression of a cDNA Encoding Human Endothelium-Derived Relaxing Factor/Nitric Oxide Synthase; The journal of Biological Chemistry (1992) vol. 267, No. 21 pp. 14519-14522.
Philip A. Marsden et al; Molecular Cloning and Characterization of Human Endothelial Nitric Oxide Synthase; FEBS Letters (1992) vol. 307, No. 3, pp. 287-293.
Masaki Nakane et al; Cloned Human Brain Nitric oxide Synthase is Highly Expressed in Skeletal Muscle; FEBS Letters (1993) vol. 316, No. 2 pp. 175-180.
David A. Geller et al; Molecular Cloning and Expression of Inducible Nitric Oxide Synthase from Human Hepatocytes; Proceedings of the National Academy of Sciences of the United States of America (1993) vol. 90, No. 8 pp. 3491-3495.
Paula A. Sherman et al; Purification and cDNA Sequence of an Inducible Nitric Oxide Synthase from a Human Tumor Cell Line; Biochemistry (1993) vol. 32, No. 43 pp. 11600-11605.
Ian G. Charles et al; Cloning, Characterization, and Expression of a cDNA Encoding an Inducible Nitric Oxide Synthase from the Human Chondrocyte; Proceeding of the National Academy of Sciences of the United States of America (1993) vol. 90, No. 23, pp. 11419-11423.
Nicole A. Chartrain et al; Molecular Cloning, Structure, and Chromosomal Localization of the Human inducible Nitric Oxide Synthase Gene; Journal of Biological Chemistry (1994) vol. 269, No. 9 pp. 6765-6772.
B. S. S. Masters et al; Neuronal Nitric Oxide Synthase, A Modular Enzyme Formed by Convergent Evolution: Structure of A Cysteine Thiolate-Liganded Heme Protein that Hydroxylates l-arginine to Produce NO as a Cellular Signal; FASEB Journal (1996) vol. 10, No. 5, pp. 552-558.
Michael A. Marletta et al; Macrophage oxidation of l-Arginine to Nitrite and Nitrate: Nitric Oxide is an Intermediate; Biochemistry (1988) vol. 27, No. 24 pp. 8706-8711.
Nyoun Soo Kwon et al; l-Citrulline Production from l-Arginine by Macrophage Nitric Oxide Synthase; The Journal of Biological Chemistry (1990) vol. 265, No. 23 pp. 13442-13445.
Bernd Mayer et al; Brain Nitric Oxide Synthase is a Biopterin- and Flavin-Containing Multi-Functional Oxido-Reductase; FEBS Letters (1991) vol. 288 pp. 187-191.
Dennis J. Stuehr et al; Nw-Hydroxy=l-Arginine is an Intermediate in the Biosynthesis of Nitric Oxide from l-Arginine; The Journal of Biological Chemistry (1991) vol. 266, No. 10 pp. 6259-6263.
Peter Klatt et al; Multiple Catalytic Functions of Brain Nitric Oxide Synthase; The Journal of Biological Chemistry (1993) vol. 268, No. 20 pp. 14781-14787.
Michael A. Marletta; Nitric Oxide Synthase: Aspects Concerning Structure and Catalysis; Cell (1994) vol. 78, No. 6 pp. 927-930.
Robert A. Pufahl et al; Oxidation of Ng-Hydroxy-l-Arginine by Nitric Oxide Synthase: Evidence for the Involvement of the Heme in Catalysis; Biochemical and Biophysical Research Communications (1993) vol. 193, No. 3 pp. 963-970.

(Continued)

*Primary Examiner*—Ralph Gitomer
(74) *Attorney, Agent, or Firm*—Michael P. Morris; Edouard G. Lebel; David A. Dow

(57) ABSTRACT

The present invention relates to a method for determining NO enzymatically and its use for the identification of substances which can modulate a nitric oxide synthase activity.

17 Claims, 1 Drawing Sheet

OTHER PUBLICATIONS

Figure 1:
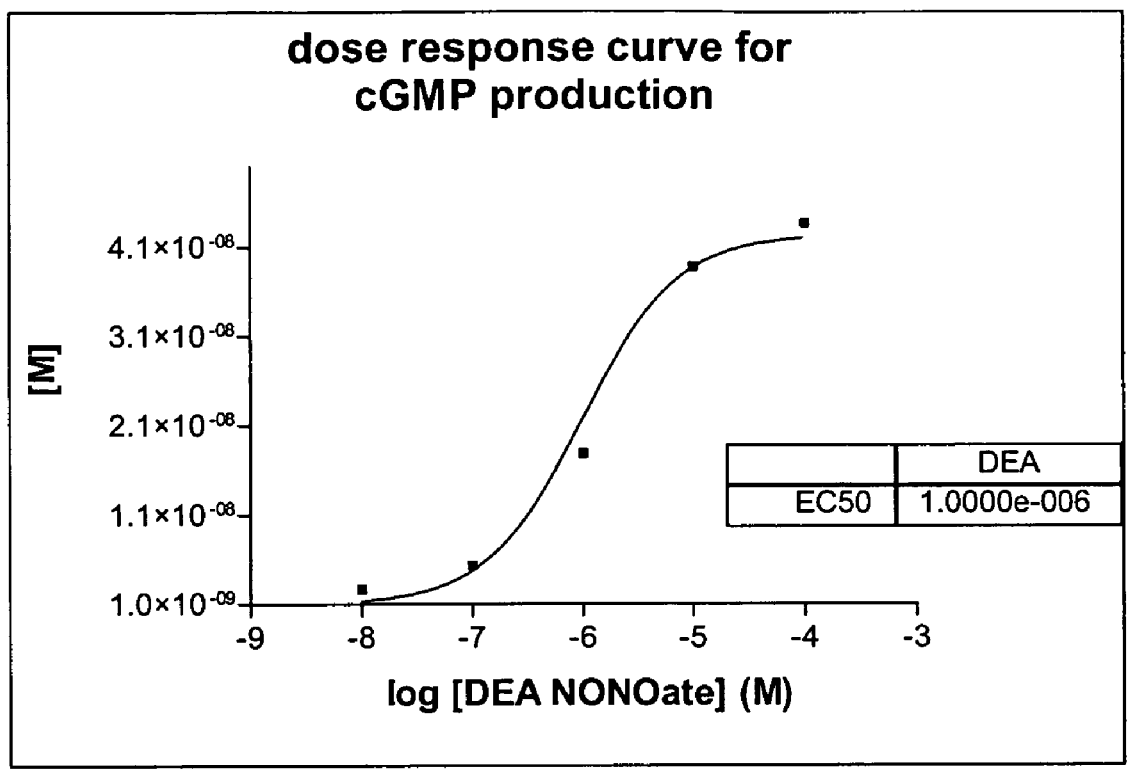

Bernd Clement et al; Cytrochrome P450 Dependent N-Hydroxylation of a Guanidine (Debrisoquine), Microsomal Catalysed Reduction and Further Oxidation of the N-Hydroxy-Guanidine Metabolite to the Urea Derivative; Biochemical Pharmacology (1993) vol. 46, No. 12 pp. 2249-2267.

Thomas P. Misko et al; A Fluorometric Assay for the Measurement of Nitrite in Biological Samples; Analytical Biochemistry (1993) vol. 214 pp. 11-16.

Rupert Gerzer et al; Soluble Guanylate Cyclase Purified from Bovine Lung Contains Heme and Copper; FEBS Letters (1981) vol. 132 p. 71.

Ulrike Zabel et al; Human Soluble Guanylate Cyclase: Functional Expression and Revised Isoenzyme Family; Biochemical Journal (1998) vol. 335 p. 51.

Dmitry N. Kosarikov et al; Human Soluble Guanylate Cyclase: Functional Expression, Purification and Structural Characterization; Archives of Biochemistry (2001) vol. 388 pp. 185-197.

Joseph S. Beckman et al; Apparent Hydroxyl Radical Production by Peroxynitrite: implications for Endothelial Injury from Nitric Oxide and Superoxide; Proceeding of the National Academy of Sciences of the United States of America (1990) vol. 87 pp. 1620-1624.

Chris M. Maragos et al; Complexes of *NO with Nucleophiles as Agents for the Controlled Biolofical Release of Nitric Oxide. Vasorelaxant EffectsI; Journal of Medicinal Chemistry (1991) vol. 34 pp. 3242-3247.

David A. Wink et al; DNA Deaminating Ability and Genotoxicity of Nitric Oxide and its Progenitors; Science (1991) vol. 254 pp. 1001-1003.

Joseph A Hrabie et al; new Nitric Oxide-Releasing Zwitterions Derived from Polyamines; Journal of Organic Chemistry (1993) vol. 58 pp. 1472-1476.

Ulla Malo-Ranta et al; Nitric Oxide Donor GEA 3162 Inhibits Endothelial Cell-Mediated Oxidation of Low Density Lipoprotein; FEBS Letters (1994) vol. 337 pp. 179-183.

Hong-Tao Ma et al; Ca2+ Entry Activated by S-Nitrosylation; the Journal of Biological Chemistry (1999) vol. 274, No. 50 pp. 35318-35324.

Masaki Nakane et al; Novel Potent and Selective Inhibitors of Inducible Nitric Oxide Synthase; Molecular Pharmacology (1995) vol. 73 pp. 831-834.

Robyn L. Rairigh et al; Role on Inducible Nitric oxide Synthase in regulation of Pulmonary Vascular tone in the Late Gestation Ovine Fetus; Journal Clinical Investigation (1998) vol. 101, No. 1 pp. 15-21.

Ana M. Briones et al; Role of iNOS in the Vasodilator Responses Induced by L-arginine in the Middle Cerebral Artery From Normotensive and Hypertensive Rats; British Journal of Pharmacology (1999) vol. 126 pp. 111-120.

C. L. Boulton et al; Nitric Oxide-Dependent Long-Term Potentiation is Blocked by a Specific Inhibitor of Soluble Guanylyl Cyclase; Neuroscience (1995) vol. 69, No. 3 pp. 699-703.

Friedrich Brunner et al; Novel Guanylyl Cyclase Inhibitor, ODQ Reveals Role of Nitric Oxide, but not of Cyclic GMP in Endothelin-1 Secretion; FEBS Letters (1995) vol. 376 pp. 262-266.

John Garthwaite et al; Potent ans Selective Inhibition of Nitric Oxide-Sensitive Guanylyl Cyclase by 1H-[1,2,4]Oxadiazolo[4,3-a]quinoxalin-1-one; Molecular Pharmacology (1995) vol. 48 pp. 184-188.

Maria A. Moro et al; cGMP Mediated the Vascular and Platelet Actions of Nitric Oxide: Confirmation Using an Inhibitor of Soluble Guanylyl Cyclase; Proc. Natl. Academy of Sciences of United States of America (1996) vol. 93 pp. 1480-1485.

Astrid Schrammel et al; Characterization of iH-[1,2,4]Oxadiazolo[4,3-a]quinoxalin-l-one-as a Heme-Site Inhibitor of Nitric Oxide-Sensitive Guanylyl Cyclase; Molecular Pharmacology (1996) vol. 50 pp. 1-5.

Najah Abi-Gerges et al; A Comparative Study of the Effects of Three Guanylyl Cyclase Inhibitors on the L-Type Ca2+ and Muscarinic K+ Currents in Frog Cardiac Myocytes; British Journal of Pharmacology (1997) vol. 127 pp. 1369-1377.

Linda J. Olson et al; Selective Guanylyl Cyclase Inhibitor Reverses Nitric Oxide-Induced Vasorelaxation; Hypertension (1997) vol. 29 pp. 254-261.

Christopher G. Sobey et al; Effects of a Novel Inhibitor of Guanylyl Cyclase on Dilator Response of Mouse Cerebral Arterioles; Stroke (1997) vol. 28 pp. 837-843.

Tsonglong Hwang et al; Comparison of Two Soluble Guanylyl Cyclase Inhibitors, Methylene Blue and ODQ, on Sodium Nitroprusside-Induced Relaxation in Guinea-Pig Trachea; British Journal of Pharmacology (1998) vol. 125 pp. 1158-1163.

Robert Motterlini et al; Endothelial Heme Oxygenase-1 Induction by Hypoxia; The Journal of Biological Chemistry (2000) vol. 275, No. 18 pp. 13613-13620.

Ichiro Sakuma et al; Identification of Arginine as a Precursor of Endothelium-Derived Relaxing Factor; Proc. Natl. Acad. Sci. USA (1988) vol. 85 pp. 8664-8667.

Edward P. Garvey et al; 1400W is a Slow, Tight Binding, and Highly Selective Inhibitor of inducible Nitric-Oxide Synthase in Vitro and in Vivo; the Journal of Biological Chemistry (1997) vol. 272, No. 8 pp. 4959-4963.

Eric Gumpricht et al; Nitric oxide Ameliorates Hydrophobic Bile Acid-Induced Apoptosis in Isolated Rat Hepatocytes by Non-Mitochondrial Pathways; The Journal of Biological Chemistry (2002) vol. 277 No. 28 pp. 25823-25830.

William M. Moore et al; 1-N6-(1-Iminoethyl)lysine: A Selective Inhibitor of Inducible Nitric Oxide Synthase; Journal Medicinal Chemical (1994) vol. 37 3886-3888.

Ferenc Laszlo et al; Actions of Isoform-Selective and Non-Selective Nitric Oxide Synthase inhibitors on Endotoxin-Induced Vascular Leakage in rat Colon; European Journal of Pharmacology (1997) vol. 334 pp. 99-102.

Lindy L. Thomsen et al; Selective Inhibition on Inducible Nitric Oxide Synthase Inhibits Tumor Growth in Vivo: Studies with 1400W, a Novel inhibitor; Cancer Research (1997) vol. 57 pp. 3300-3304.

Loan N. Miller et al; A-350619: A Novel Activator of Soluble Guanylyl Cyclase; Life Sciences (2003) vol. 72 pp. 1015-1025.

Louis J. Ignarro; Role of Nitric Oxide in the Pathophysiology of Hypertension: Physiology and Pathophysiology of Nitric oxide; Kidney International (1996) vol. 49, Suppl. 55 pp. 2-5.

John R. Vane et al; Inducible Isoforms of Cyclooxygenase and Nitric-Oxide Synthase in Inflammation; Proc. Natl. Acad. Sci. USA (1994) vol. 91 pp. 2046-2050.

Kai Y. Xu et al; Nitric Oxide Synthase in Cardiac Sarcoplasmic Reticulum; Proc. Natl. Acad. Sci. USA (1999) vol. 96 pp. 657-662.

Gunter Schultz et al; GTP Pyrophosphaste-lyase (cyclizing), EC 4,6,1,2; Guanylate Cyclase; pp. 379-389, no date given.

Yu-Chen Lee et al; Human Recombinant Soluble Guanylyl Cyclase: Expression, Purification, and Regulation; PNAS (2000) vol. 97, No. 20 pp. 10763-10768.

E. Moilanen et al; Inhibition by Nitric Oxide-Donors of Human Polymorphonuclear Leucocyte Functions; British Journal Pharmacology (1993) vol. 109 pp. 852-858.

Eric Southam et al; The Nitric Oxide-Cyclic GMP Pathway and Synaptic Plasticity in the rat Superior Cervical Ganglion; British Journal Pharmacology (1996) vol. 119 pp. 527-532.

Daryl D. Rees et al; A Specific Inhibitor of Nitric Oxide Formation from 1-Arginine Attenuates Endothelium-Dependent Relaxation; British Journal Pharmacology (1989) vol. 96 pp. 418-424.

Rainer Maier et al; Inducible Nitric Oxide Synthase from Human Articular Chondrocytes: cDNA Cloning and Analysis of mRNA Expression; Biochimica et Biophysica Acta (1994) vol. 1208 pp. 145-150.

Markus Hoenicka et al; Purified Soluble Guanylyl Cyclase Expressed in a Baculovirus/Sf9 System: Stimulation by YC-1, Nitric oxide, and Carbon Monoxide; Journal of Molecular Medicinal (1999) vol. 77 pp. 14-23.

Russell S. Drago et al; The Reaction of Nitrogen(II) Oxide with Various Primary and Secondary Amines; JACS (1961) vol. 83 pp. 1819-1822.

Russell S. Drago et al; The reaction of Nitrogen(II) Oxide with Diethylamine; JACS (1960) vol. 82 pp. 96-98.

Owen W. Griffith et al; Nitric Oxide Synthases: Properties and Catalytic Mechanism; Annual Review of Physiology (1995) vol. 57 pp. 707-736.

Bernd Mayer; Biochemistry and Molecular Pharmachology of Nitric Oxide Synthases, in Nitric Oxide in the Nervous System (Steven R. Vincent Edition); Academic; New York 1995.

Tim Corell et al; Pharmacology of Mesoionic Oxatriazole Derivatives in Blood, Cardiovascular and Respiratory Systems; Pol. Journal of Pharmacology (1994) vol. 46 pp. 553-566.

Gunnar Karup et al; Mesoionic Oxatriazole Derivatives—A New Group of No-Donors; Pol. Journal of Pharmacology (1994) vol. 46 pp. 541-552.

Paul L. Feldman et al; The Surprising Life of Nitric Oxide; Chemical Engineering News (1993) vol. 71 pp. 26-38.

Jadwiga Robak et al; Scavenging of Superoxide Anions by Nitric Oxide Donors; Pharmacological Research (1992) vol. 25, Suppl. 2 pp. 355-356.

Bernard B. Keele et al; Superoxide Dismutase from *Escherichia coli* B; The Journal of Biological Chemistry (1970) vol. 245; No. 22 pp. 6176-6181.

Guenter Schultz and Eycke Boehme; Guanylate Cyclase; GTP pyrophosphate-lyase (cyclizing), EC 4,6,1,2; in Methods of Enzymatic Analysis (1984) (Bergmeyer, Bergmeyer and Grass, eds) pp. 379-389, Verlang Chemie.

* cited by examiner

DETECTION OF NO BY USING GUANYLYL CYCLASE AND CGMP PRODUCTION AS A READOUT SYSTEM

RELATED APPLICATIONS

Benefit of U.S. Provisional Application Ser. No. 60/529,203, filed on Dec. 12, 2003 and of European Patent Application 03 027 159, filed on Nov. 26, 2003 are hereby claimed, and which applications are incorporated herein in their entireties.

INTRODUCTION

The L-arginine-nitric oxide pathway is involved in a large variety of physiological processes (Mayer; B. et al., 1997; Vallance, P. et al., 2002; Wendy, K. et al., 2001), like for example the regulation of blood pressure, platelet aggregation or host defence against pathogens. Nitric oxide (NO) can be for example produced by nitric oxide synthase (NOS) representing a group of enzymes existing as three different isoforms of NOS: eNOS, nNOS and iNOS (Janssens, S. P. et al., 1992; Marsden, P. A. et al., 1992; Nakane, M. et al., 1993; Geller, D. A. et al., 1993; Sherman, P. A. et al. 1993; Charles, I. G. et al., 1993; Maier, R. et al., 1994; Chartrain, N. A. et al., 1994).

To influence diseases which are associated with NOS activity (e.g. chronic obstructive pulmonary disease (COPD), arteriosclerosis, wound-heeling) modulation of NOS activity is wanted. Therefore, there exists a need for substances which can modulate NOS activity. Subsequently, there is a need for e.g. an ultra high throughput compatible assay which is sensitive enough to determine whether a substance can modulated NOS activity.

In the following the known reaction of NOS with Arginine in presence of NADPH, FAD, FMN and biopterin resulting in Citrulline and No and NADP$^+$ is given (Griffith, O. W. et al, 1995; Mayer, B. et al.; 1995; Stuehr, D. J. et al., 1991; Klatt, P. et al., 1993; Feldmann, P. L. et al, 1993; Marletta, M. A., et al., 1994; Pufahl, R. A. et al., 1993; Clement, B. et al., 1993):

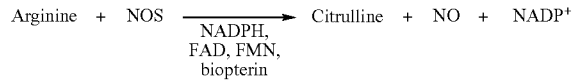

To verify whether NOS activity indeed has been altered it is essential to measure NOS activity. To measure the activity of a NOS enzyme it is necessary to detect arginine consumption, citrulline production or NO generation.

Currently, only assay systems which are not compatible to miniaturized high through put screening systems are known. Only radioactive systems for measuring arginine or citrulline are available. To make matters worse, said systems are only meaningful at high doses of arginine or citrulline and therewith respective miniaturising is not successfully possible.

Other systems are not usable for a screening campaign since a substance to be tested interacts unspecifically with substances of the system (Powell D. and Williams D., 2002).

Since NO is only stable for a few seconds it is not regarded as a suitable read-out. Commercially available NO detection systems have been failed as a suitable readout technique in high throughput screening (Misko T. P. et al. 1993).

For a high throughput compatible NOS activity assay for a drug screening campaign it is necessary to have a sensitive and miniaturizable assay format.

DESCRIPTION OF THE INVENTION

Until now nitric oxide (NO) was regarded as a not suitable readout since it is only stable for a few seconds. The present invention provides for a method for detecting NO which is surprisingly accessible to a new detection method of the present invention.

The guanylyl cyclase is a physiological target for NO. Guanylyl cyclase becomes activated by NO several hundred fold. In the presence of GTP a said activated guanylyl cyclase catalyses the generation of cGMP. Therewith, NO causes the generation of cGMP. As disclosed in the present invention said signal transduction can be surprisingly used in an inverse direction to detect NO quantitatively.

We have established a high throughput compatible assay format for the detection of Nitric oxide synthase (NOS) activity employing guanylyl cyclase and cGMP as an amplification and readout system for the detection of NO. Our assay setup is as follows: recombinantly expressed NOS enzyme, purified NOS enzyme from a natural source or working with a cell based assay system containing NOS is used to generate NO. Adding soluble guanylyl cyclase to the system leads to an increased activation of the guanylyl cyclase enzyme. This results in the generation of cyclic GMP which is then detected using a cGMP detection system. As a cGMP detection system e.g. commercially available detection systems can be used.

This detection system for NO is quite sensitive since the activation of the guanylyl cyclase results in an cGMP increase. One activated guanylyl cyclase can generate several cGMP molecules therefore we have an amplification effect and can overcome the sensitivity issue.

The present invention provides therewith a technical basis for a long felt need: An assay for determining whether a substance can modulate NOS activity. Therewith the invention also provides for a high throughput screening (HTS) compatible NOS activity assay for a drug screening campaign.

Nitric oxide synthase (NOS) according to the present invention is any enzyme which is selected from a group consisting of: i-NOS (inducible NO synthase, II) e-NOS (endothelial NO synthase, III), and n-NOS (neuronal NO synthase, I).

Nitric oxide synthase (NOS) activity according to the present invention is an activity which catalyzes the formation of NO by converting arginine to citrulline with the concomitant release of NO. NOS activity according to the present invention includes any further conversion of any other substrate resulting in the generation of NO.

A substrate according to the invention is every substance which can be transformed by NOS in any other substance as long as NO is produced. A preferred substance of the invention is arginine.

A substance to be tested to be a modulator of NOS according to the invention is any small chemical molecule, peptide, or antibody.

A modulator according to the invention is either an inhibitor of the invention or an activator of the invention.

An inhibitor of the nitric oxide synthase activity according to the present invention is identifiable by an reduced level of cGMP in a method according to the invention which can be measured in the solution to which the substance to be tested (in step (c)) was added.

An activator of the nitric oxide synthase activity according to the present invention is identifiable by an enhanced level of cGMP in a method according to the invention which can be measured in the solution to which the substance to be tested (in step (c)) was added.

A method according to the invention is, wherein the method comprises:
providing a solution comprising NO;
adding guanylyl cyclase and guanosin triphosphate (GTP) under conditions which allow synthesis of cyclic guanosin monophosphate (cGMP);
measuring cGMP. Measuring according to the invention is any suitable detecting method which is useful of determining cGMP quantitatively. A preferred method for measuring cGMP according to the invention uses an antibody which is capable of binding to cGMP.

Said method can be used to detect NO in solution.

Said method can additionally be used in a high throughput screening. Therefore, the present invention provides for a method for detection of nitric oxide (NO)) in an high throughput (HTS) format wherein the above mentioned method is performed. Said method can be performed by using a plate having at least 96 wells, more preferred is the use of a 384 well plate or a 1536 well plate. Also preferred is the use of a chip as reaction and/or readout platform.

In one embodiment the present invention provides for a method for measuring nitric oxide synthase activity, wherein the method comprises:
(a) providing a solution comprising a nitric oxide synthase and a suitable substrate under conditions which allow synthesis of nitric oxide;
(b) adding guanylyl cyclase and GTP under conditions which allow synthesis of cGMP;
(c) measuring cGMP.

Measuring cGMP according to the invention is any suitable detecting method which is useful of determining cGMP quantitatively. A preferred method for measuring cGMP according to the invention uses an antibody which is capable of binding to cGMP. Said method can be used in a high throughput screening. Therefore, the present invention provides for a method for measuring nitric oxide synthase (NOS) activity in an high throughput (HTS) format wherein the above mentioned method is performed. Said method can be performed by using a plate having at least 96 wells, more preferred is the use of a 384 well plate or a 1536 well plate. Also preferred is the use of a chip as reaction and/or readout platform.

In a further embodiment the present invention provides for a method for determining whether a substance is modulator of nitric oxide synthase activity according to the invention, wherein the method comprises:
(a) providing a first solution comprising a nitric oxide synthase and a suitable substrate under conditions which allow synthesis of nitric oxide;
(b) providing a second solution comprising a nitric oxide synthase and a suitable substrate under conditions which allow synthesis of nitric oxide;
(c) adding a substance to be tested to the first or the second solution;
(d) adding guanylyl cyclase and GTP under conditions which allow synthesis of cGMP to the first and the second solution;
(e) measuring cGMP in the first and the second solution;
(f) comparing cGMP levels of the first and the second solution, wherein a modulator of a nitric oxide synthase activity is identified by different levels of cGMP.

Measuring cGMP according to the invention is any suitable detecting method which is useful of determining cGMP quantitatively. A preferred method for measuring cGMP according to the invention uses an antibody which is capable of binding to cGMP. Said method can be used in a high throughput screening. Therefore the present invention provides for a method for determining whether a substance is modulator of nitric oxide synthase (NOS) activity in an high throughput (HTS) format wherein the above mentioned method is performed. Said method can be performed by using a plate having at least 96 wells, more preferred is the use of a 384 well plate or a 1536 well plate. Also preferred is the use of a chip as reaction and/or readout platform.

In a further embodiment all above mentioned methods of to the invention additionally comprise superoxid dismutase (SOD) which can be added together with guanylyl cyclase and GTP.

All methods of the present invention can be used in a high throughput screening assays.

The present invention also provides for a kit for determining whether a substance is a modulator—i.e. an activator or an inhibitor—of NOS activity comprising: guanylyl cyclase, GTP and a system for detection of cGMP. Said system is any suitable detecting method which is useful of determining cGMP quantitatively. A preferred method for measuring cGMP according to the invention uses an antibody which is capable of binding to cGMP.

In a more preferred embodiment said kit of the invention further comprises Superoxide dismutase (SOD).

In a most preferred embodiment said kit of the invention further comprises nitric oxid synthase (NOS) which is selected from a group consisting of: i-NOS, e-NOS, and n-NOS. This kit can additionally comprise Superoxide dismutase (SOD).

In a further embodiment the present invention also provides for a kit for measuring nitric oxide synthase (NOS) activity comprising: guanylyl cyclase, GTP and a system for detection of cGMP. Said system is any suitable detecting method which is useful of determining cGMP quantitatively. A preferred method for measuring cGMP according to the invention uses an antibody which is capable of binding to cGMP.

In a more preferred embodiment said kit of the invention further comprises Superoxide dismutase (SOD).

In a most preferred embodiment said kit of the invention further comprises nitric oxid synthase (NOS) which is selected from a group consisting of: i-NOS, e-NOS, and n-NOS. This kit can additionally comprise Superoxide dismutase (SOD).

The present invention additionally provides for a further kit for detection of nitric oxid (NO) comprising: guanylyl cyclase, GTP and a system for detection of cGMP. Said system is any suitable detecting method which is useful of determining cGMP quantitatively. A preferred method for measuring cGMP according to the invention uses an antibody which is capable of binding to cGMP.

In a more preferred embodiment said kit of the invention further comprises Superoxide dismutase (SOD).

The following Examples are meant to illustrate the present invention, however, shall not be construed as limitation. However, the Examples describe most preferred embodiments of the invention.

EXAMPLES

Example 1

Assay Description

Detection of NOS activity by using the activation of soluble guanylyl cyclase, an enzyme which is well known for years (Gerzer R., et al. 1981; Zabel U., et al., 1998; Hoenicka, M. et al., 1999; Lee, Y. C. et al., 2000; Kosarikov, D. N. et al.; 2001). NO produced by the different NOS enzymes can activate soluble guanylyl cyclase and also its membrane standing counterpart. In said type of assays recombinantly expressed NOS, a cell-lysate containing NOS as well as NOS purified from a natural source can be used (Janssens, S. P. et al., 1992; Marsden, P. A. et al., 1992; Nakane, M. et al., 1993; Geller, D. A. et al., 1993; Sherman, P. A. et al. 1993; Charles, I. G. et al., 1993; Maier, R. et al., 1994; Chartrain, N. A. et al., 1994).

Here we describe a non radioactive HTS compatible assay format which can be used to detect the NO produced by the NOS activity via activation of guanylyl cyclase and subsequent detection of the produced cGMP using the AlphaScreen technology in a mix and measure mode.

Arginine as a substrate is converted by each of the three different NOS enzymes respectively, into citrulline. During this process NO is also produced. Therefore NO detection can be used to monitor directly the activity NOS enzymes. It is known that NO can directly stimulate the soluble guanylyl cyclase. This activation leads to an increase in cGMP production by the activated guanylyl cyclase. The produced cGMP can be detected and quantified. A variety of different technologies can be employed for the detection and quantification of the newly produced cGMP. This technologies can be e.g. based on HTRF (Claret E. J., et al., 2004) or radioactivity (Perkin Elmer: Flashplate cyclic cGMP [$^{125}$I]-assay product no: SMP002J001PK) or like it is shown here based on the AlphaScreen technology. Using the Alphascreen cGMP competition assay a biotinylated cGMP is used to generate a fluorescence signal. The biotinylated cGMP is binding to the AlphaScreen donor bead via streptavidin and is binding to the AlphaScreen acceptor bead via an anti-cGMP specific antibody bound to the bead surface. If cGMP is freshly produced by the stimulated guanylyl cyclase it is competing with the binding to the anti-cGMP antibody. Therefore, the standard fluorescence signal is getting reduced by freshly produced cGMP, which is not biotinylated.

Example 2

Standard Operating Procedure for Performing a Mix and Measure HTS Compatible NOS Activity Assay Method In 384-well plates, 3 µl of a test compound diluted in distilled water (final concentration of compounds 5 µg/ml; DMSO 1%) is mixed with 3 µl enzyme mix dissolved in assay buffer (i-NOS final 2-10 µg/ml or e-NOS final 2-10 µg/ml or n-NOS final 2-10 µg/ml, sGC final 1:800 000—given amounts of respective NOS enzymes are based on total concentration of cell culture supernatant employed (insect cell recombinant expression system)). After an incubation time of 30 minutes 3 µl substrate mix dissolved in assay buffer (GTP final 100 µM, Arginine final 3 µM, NADPH final 500 µM, for n-NOS 1 µM Ca$^{2+}$ and 1 µM Calmodulin is necessary) is added. After another incubation time of 90 minutes the reaction is stopped with 10 µl acceptor and donor bead-antibody mix dissolved in stop/detection buffer (final concentration of each bead-type 15 µg/ml; antibody final 1:15000).

After an overnight incubation, the assay is measured using e.g. an Alphaquest reader (Perkin Elmer), which is measuring fluorescence at 520-620 nm.

Assay buffer: 25 mM Tris pH 7.4, 3 mM MgCl$_2$, 3 mM DTT, 0.05% BSA, 3 µM BH$_4$, 1M FAD, 1M FMN, 10 µM 4-{[3',4'-(Methylenedioxy)benzyl]amino}-6-methoxyquinazoline Stop/detection buffer: 50 mM Tris, 50 mM EDTA pH 7.4, 0.10% BSA, 0.10% Tween-20

Each assay microtiter plate contains wells with vehicle control instead of compound (1% DMSO in water) as reference for non-inhibited enzyme activity (100% CTL; high values) and wells with 100 µM AMT as reference for inhibited enzyme activity (0% CTL; low values).

Each assay micro-titer plate contains a cGMP standard curve (1, 10, 100, 1000, 3000, 10000, 100000, 1000000 pM/l) in duplicate used as reference to calculate the amount of cGMP produced in every well.

The analysis of the data is performed by the calculation of the percentage of cGMP in the presence of the test compound compared to cGMP generated from the positive control:

(cGMP(sample)−cGMP (low value))×100/(cGMP (high value)−cGMP (low value))

An inhibitor of the enzyme activity will give values between 100% Ctl (no inhibition) and 0% Ctl (complete inhibition).

Materials used are well known in the art, however, in the following respective suppliers are given: The 384 low volume plates were purchased from Greiner (white; cat.-no. 784075). The AlphaScreen IgG Detection Kit (cat.-no. 6760617) and the biotinylated cGMP were bought from Perkin Elmer. The anti-cGMP antibody (cat.-no. 970161) is from Merck Biosciences. The different NOS enzymes i-NOS (cat.-no. 201-069), e-NOS (cat.-no. 201-070) and n-NOS (cat.-no. 201-068), sGC (cat.-no. 201-177) and the L-Arginine (cat.-no. 101-004) were from Alexis. The NADPH (cat.-no. N-6005) and the GTP (cat.-no. G-5884) were purchased from Sigma. All other materials were of highest grade commercially available.

Example 3

Standard Operating Procedure for Performing a Mix and Measure HTS Compatible NOS Activity Assay Optimized by Adding a Further Enzyme to the Reaction Mixture the Superoxide Dismutase (SOD)

In the following a further variant of the assay of the invention is disclosed in which an enzyme has been added to the reaction mixture. The Superoxide dismutase (SOD) (Keele Jr. B. B. et al., 1970; Beckman J. S. et al., 1990) increases the sensitivity of the assay system and therefore reduces the amount of NOS enzyme needed for performing the assay.

Method

In the 384-well plates, 3 µl of the test compounds diluted in distilled water (final concentration of compounds 5 µg/ml; DMSO 1%) is mixed with 3 µl enzyme mix dissolved in assay buffer (i-NOS final 2 µg/ml, e-NOS 5 µg/ml, n-NOs 0.4 µg/ml, SOD final 300 nM, sGC final 1:800 000—given amounts of respective NOS enzymes are based on total concentration of cell culture supernatant employed (insect cell recombinant expression system)). After an incubation time of 30 minutes 3 µl substrate mix dissolved in assay buffer (GTP final 100 µM, Arginine final 3 µM, NADPH final 500 µM, for nNOS 1 µM Ca$^{2+}$ and 1 µM Calmodulin is necessary) is added. After another incubation time of 90 minutes the reaction is stopped with 10 µl acceptor and donor bead-antibody mix dissolved in stop/detection buffer (final concentration of each bead-type 15 µg/ml; antibody final 1:15000).

After an overnight incubation, the assay is measured using e.g. an Alphaquest (as outlined in Example 2).

Assay buffer: 25 mM Tris pH 7.4, 3 mM MgCl$_2$, 3 mM DTT, 0.05% BSA, 3 µM BH$_4$, 1 µM FAD, 1 µM FMN, 10 µM 4-{[3',4'-(Methylenedioxy)benzyl]amino}-6-methoxyquinazoline Stop/detection buffer: 50 mM Tris, 50 mM EDTA pH 7.4, 0.10% BSA, 0.10% Tween-20

Each assay microtiter plate contains wells with vehicle control instead of compound (1% DMSO in water) as reference for non-inhibited enzyme activity (100% CTL; high values) and wells with 100 µM AMT as reference for inhibited enzyme activity (0% CTL; low values).

Each assay microtiter plate contains a cGMP standard curve (1, 10, 100, 1000, 3000, 10000, 100000, 1000000 pM/l) in duplicate used as reference to calculate the amount of cGMP produced in every well.

The analysis of the data is performed by the calculation of the percentage of cGMP in the presence of the test compound compared to cGMP generated from the positive control.

(cGMP(sample)−cGMP (low value))×100/(cGMP (high value)−cGMP (low value))

An inhibitor of the enzyme activity will give values between 100% Ctl (no inhibition) and 0% Ctl (complete inhibition).

Example 4

Stimulation of Soluble Guanylyl Cyclase and Subsequent cGMP Detection

The principle mechanism of the stimulation of the soluble guanylyl cyclase can be shown by using a NO donor compound like for example DEA NONOate or others like DETA NONOate, DPTA NONOate, GEA 5024 or GEA 3162 (Drago R. S. & Paulik F. E., 1960; Drago R. S. & B. R. Karstetter B. R. 1961; Maragos, C. M. et al, 1991; Wink D. A., et al. 1991; Hrabie, et al. 1993; Robak, et al., 1992; Moilanen, E. et al. 1993; Corell, T. et al. 1994; Karup, G. et al. 1994; Malo-Ranta, U. et al. 1994; Ma H. T. et al. 1999). These type of compounds produce NO which can stimulate the soluble guanylyl cyclase which leads to a cGMP production. FIG. 1 shows the cGMP production after stimulating the soluble guanylyl cyclase with DEA NONOate in a dose dependent manner. For detection of cGMP an AlphaScreen competition assay was used.

Example 5

Inhibition of Different NOS Enzymes Using Standard Inhibitors

| enzyme | AMT [µM] | ODQ [µM] | L-NMMA [µM] | 1400W [µM] | L-NIL [µM] |
|---|---|---|---|---|---|
| iNOS | $1.3 \times 10^{-8}$ | $7.7 \times 10^{-7}$ | $3.2 \times 10^{-6}$ | $9.7 \times 10^{-7}$ | $2.2 \times 10^{-6}$ |
| eNOS | $9.9 \times 10^{-8}$ | $5.8 \times 10^{-7}$ | $2.3 \times 10^{-6}$ | $2.0 \times 10^{-4}$ | $2.7 \times 10^{-5}$ |
| nNOS | $3.1 \times 10^{-8}$ | $9.0 \times 10^{-7}$ | $7.9 \times 10^{-6}$ | $1.5 \times 10^{-5}$ | $2.8 \times 10^{-4}$ |

In Table 1 is given: IC50 [µM] determination of different compounds for the different NOS enzymes.

Above mentioned NOS inhibitors are state of the art as depicted below:

AMT: Nakane, M. et al., 1995; Tracey, W. R. et al., 1995; Rairigh, R. L. et al. 1998; Briones, A-M. et al., 1999;

ODQ: Boulton, C. L. et al., 1995; Brunner, F. et al., 1995; Garthwaite, J et al., 1995; Moro, M. A. et al., 1996; Schrammel, A. et al., 1996; Southam, E. et al., 1996; Abi-Gerges, N. et al., 1997; Olson, L. J, et al., 1997; Sobey C. G. & Faraci F. M. 1997; Hwang, T. L. et al., 1998; R. Motterlini, et al., 2000;

L-NMMA: Sakuma, I. et al., 1988; Rees, D. D. et al., 1989;

1400W: Garvey, E. P et al., 1997; Thomsen, L. L. et al., 1997; Laszlo F. & Whittle B. J. R, 1997; Gumpricht, E. et al., 2002;

L-NIL: Moore, W. M. et al., 1994.

Literature

Meyer B. and Hemmens B. (1997) Biosynthesis and action of nitric oxide in mammalian cells Trends Biochem. Sci. 22, 477-481

Patrick Vallance and James Leiper: Blocking NO Synthesis: How, where and why? Nature Reviews/Drug Discovery, Volume 1 Dec. 2002, 939-950

Wendy K. Alderton, Chris E. Cooper and Richard G. Knowles: Nitric oxide synthases: structure, function and inhibition Biochem. J. (2001) 357, 593-615

Janssens S P. Shimouchi A. Quertermous T. Bloch D B. Bloch K D. Cloning and expression of a cDNA encoding human endothelium-derived relaxing factor/nitric oxide synthase. Journal of Biological Chemistry 267(21):14519-22, 1992 Jul. 25.

Marsden P A. Schappert K T. Chen H S. Flowers M. Sundell C L. Wilcox J N. Lamas S. Michel T. Molecular cloning and characterization of human endothelial nitric oxide synthase. FEBS Letters. Vol. 307(3)(pp 287-293), 1992.

Nakane M. Schmidt HHHW. Pollock J S. Forstermann U. Murad F. Cloned human brain nitric oxide synthase is highly expressed in skeletal muscle. FEBS Letters. Vol. 316(2)(pp 175-180), 1993.

Geller D A. Lowenstein C J. Shapiro R A. Nussler A K. Di Silvio M. Wang S C. Nakayama D K. Simmons R L. Snyder S H. Billiar T R. Molecular cloning and expression of inducible nitric oxide synthase from human hepatocytes. Proceedings of the National Academy of Sciences of the United States of America. Vol. 90(8)(pp 3491-3495), 1993.

Sherman P A. Laubach V E. Reep B R. Wood E R. Purification and cDNA sequence of an inducible nitric oxide synthase from a human tumor cell line. Biochemistry. Vol. 32(43) (pp 11600-11605), 1993.

Charles I G. Palmer R MJ. Hickery M S. Bayliss M T. Chubb A P. Hall V S. Moss D W. Moncada S. Cloning, characterization, and expression of a cDNA encoding an inducible nitric oxide synthase from the human chondrocyte. Proceedings of the National Academy of Sciences of the United States of America. Vol. 90(23)(pp 11419-11423), 1993.

Maier R. Bilbe G. Rediske J. Lotz M. Inducible nitric oxide synthase from human articular chondrocytes: cDNA cloning and analysis of mRNA expression. Biochimica et Biophysica Acta—Protein Structure & Molecular Enzymology. Vol. 1208(1)(pp 145-150), 1994.

Chartrain N A. Geller D A. Koty P P. Sitrin N F. Nussler A K. Hoffman E P. Billiar T R. Hutchinson N I. Mudgett J S. Molecular cloning, structure, and chromosomal localization of the human inducible nitric oxide synthase gene. Journal of Biological Chemistry. Vol. 269(9)(pp 6765-6772), 1994.

Griffith O W. Stuehr D J. Nitric oxide synthases: Properties and catalytic mechanism. Annual Review of Physiology. Vol. 57(pp 707-736), 1995

Mayer, B.: Biochemistry and molecular pharmacology of nitric oxide synthases, in Nitric Oxide in the Nervous System (S. R. Vincent, ed.), Academic, New York, 21-42, 1995

Masters B SS. McMillan K. Sheta E A. Nishimura J S. Roman L J. Martasek P. Neuronal nitric oxide synthase, a modular enzyme formed by convergent evolution: Structure studies of a cysteine thiolate-liganded heme protein that hydroxylates L-arginine to produce NO. as a cellular signal. FASEB Journal. Vol. 10(5)(pp 552-558), 1996.

Marletta M A. Yoon P S. Iyengar R. Leaf C D. Wishnok J S. Macrophage oxidation of L-arginine to nitrite and nitrate: Nitric oxide is an intermediate. Biochemistry. Vol. 27(24) (pp 8706-8711), 1988.

Kwon N S. Nathan C F. Gilker C. Griffith O W. Matthews D E. Stuehr D J. L-Citrulline production from L-arginine by macrophage nitric oxide synthase. The ureido oxygen derives from dioxygen. Journal of Biological Chemistry. Vol. 265(23)(pp 13442-13445), 1990.

Mayer B. John M. Heinzel B. Werner E R. Wachter H. Schultz G. Bohme E. Brain nitric oxide synthase is a biopterin- and flavin-containing multi-functional oxido-reductase. FEBS Letters. Vol. 288(1-2)(pp 187-191), 1991.

Stuehr D J. Kwon N S. Nathan C F. Griffith O W. Feldman P L. Wiseman J. N(omega)-hydroxy-L-arginine is an intermediate in the biosynthesis of nitric oxide from L-arginine. Journal of Biological Chemistry. Vol. 266(10)(pp 6259-6263), 1991.

Klatt P. Schmidt K. Uray G. Mayer B. Multiple catalytic functions of brain nitric oxide synthase. Biochemical characterization, cofactor-requirement, and the role of N(omega)-hydroxy-L-arginine as an intermediate. Journal of Biological Chemistry. Vol. 268(20)(pp 14781-14787), 1993.

Feldmann P L. Griffith O W. And Stuehr D J.: The surprising life of nitric oxide. Chem. Eng. News 71, 26-38, 1993

Marletta M A. Nitric oxide synthase: Aspects concerning structure and catalysis. Cell. Vol. 78(6)(pp 927-930), 1994.

Pufahl R A. Marletta M A. Oxidation of N(G)-hydroxy-L-arginine by nitric oxide synthase: Evidence for the involvement of the heme in catalysis. Biochemical & Biophysical Research Communications. Vol. 193(3)(pp 963-970), 1993.

Clement B. Schultze-Mosgau M-H. Wohlers H. Cytochrome P450 dependent N-hydroxylation of a guanidine (debrisoquine), microsomal catalysed reduction and further oxidation of the N-hydroxy-guanidine metabolite to the urea derivative. Similarity with the oxidation of arginine to citrulline and nitric oxide. Biochemical Pharmacology. Vol. 46(12)(pp 2249-2267), 1993.

Powell D., Williams D. Nitric Oxide Synthase Screening Kit for the detection of inhibitors of NOS enzyme activity Life Science News, 2002 Amersham Biosiences Misko T. P., Schilling R. J., Salvemini D., Moore W. M., Currie M. G. A; A Fluorometric Assay for the Measurement of Nitrate in Biological Samples Analytical Biochemistry 214, 11-16 1993

Gerzer R., et al.; Soluble guanylate cyclase purified from bovine lung contains heme and copper; FEBS Lett. 132, 71 (1981)

Zabel U., et al.; Human soluble guanylate cyclase: functional expression and revised isoenzyme family; Biochem. J. 335 (Pt 1), 51 (1998)

Hoenicka, M. et al.; Purified soluble guanylyl cyclase expressed in a baculovirus/Sf9 system: stimulation by YC-1, nitric oxide, and carbon monoxide; J. Mol. Med. 77, 14 (1999)

Lee, Y. C. et al.; Human recombinant soluble guanylyl cyclase: expression, purification, and regulation; PNAS 97, 10763 (2000)

Kosarikov, D. N. et al.; Human soluble guanylate cyclase: functional expression, purification and structural characterization; Arch. Biochem. Biophys. 388, 185 (2001)

Claret E. J., et al.; A new HTRF cGMP assay for monitoring Guanylyl cyclase activity; Poster presentation at the SBS Meeting in Orlando (2004)

Perkin Elmer: Flashplate cyclic cGMP [$^{125}$I]-assay product no: SMP002J001PK Keele, B. B. Jr. et al.; Superoxide Dismutase from *Escherichia coli* B; JBC Vol.245, No. 22, pp 6176-6181 (1970).

Beckman J. S. et al.; Apparent hydroxyl radical production by peroxynitrite: Implications for endothelial injury from nitric oxide and superoxide; Proc. Natl. Acad. Sci USA Vol 87, pp. 1620-1624 (1990).

Drago R. S. & Paulik F. E.; The Reaction of Nitrogen(II) Oxide with Diethylamine; JACS 82, 96 (1960)

Drago R. S. & B. R. Karstetter B. R.; The Reaction of Nitrogen(II) Oxide with Various Primary and Secondary Amines; JACS 83, 1819 (1961)

Maragos, C. M. et al.; Complexes of NO with nucleophiles as agents for the controlled biological release of nitric oxide. Vasorelaxant effects; J. Med. Chem. 34, 3242 (1991)

Wink D. A., et al.; DNA deaminating ability and genotoxicity of nitric oxide and its progenitors; Science 254, 1001 (1991)

Hrabie, et al.; New nitric oxide-releasing zwitterions derived from polyamines; JOC 58, 1472 (1993)

Robak, et al.; Pharmacol. Res. 25 S2, 355 (1992)

Moilanen, E: et al.; Inhibition by nitric oxide-donors of human polymorphonuclear leucocyte functions; Br. J. Pharmacol. 109, 852 (1993)

Corell, T. et al.; Pharmacology of mesoionic oxatriazole derivatives in blood, cardiovascular and respiratory systems; Pol. J. Pharmacol. 46, 553 (1994)

Karup, G. et al.; Mesoionic oxatriazole derivatives—a new group of NO-donors; Pol. J. Pharmacol. 46, 541 (1994)

Malo-Ranta, U. et al.; Nitric oxide donor GEA 3162 inhibits endothelial cell-mediated oxidation of low density lipoprotein; FEBS Lett. 337, 179 (1994)

Ma, H. T. et al.; Ca(2+) entry activated by S-nitrosylation. Relationship to store-operated ca(2+) entry; J. Biol. Chem. 274, 35318 (1999)

Nakane, M. et al.; Novel potent and selective inhibitors of inducible nitric oxide synthase; Mol. Pharmacol. 47, 831 (1995)

Tracey, W. R. et al.; In vivo pharmacological evaluation of two novel type II (inducible) nitric oxide synthase inhibitors; Can. J. Physiol. Pharmacol. 73, 665 (1995)

Rairigh, R. L. et al.; Role of inducible nitric oxide synthase in regulation of pulmonary vascular tone in the late gestation ovine fetus; J. Clin. Invest. 101, 15 (1998)

Briones, A-M. et al.; Role of iNOS in the vasodilator responses induced by L-arginine in the middle cerebral artery from normotensive and hypertensive rats; Br. J. Pharmacol. 126, 111 (1999)

Boulton, C. L. et al.; Nitric oxide-dependent long-term potentiation is blocked by a specific inhibitor of soluble guanylyl cyclase; Neuroscience 69, 699 (1995)

Brunner, F. et al.; Novel guanylyl cyclase inhibitor, ODQ reveals role of nitric oxide, but not of cyclic GMP in endothelin-1 secretion; FEBS Lett. 376, 262 (1995)

Garthwaite, J et al.; Potent and selective inhibition of nitric oxide-sensitive guanylyl cyclase by 1H-[1,2,4]oxadiazolo [4,3-a]quinoxalin-1-one; Mol. Pharmacol. 48, 184 (1995)

Moro, M. A. et al.; cGMP mediates the vascular and platelet actions of nitric oxide: confirmation using an inhibitor of the soluble guanylyl cyclase; PNAS 93, 1480 (1996)

Schrammel, A. et al.; Characterization of 1H-[1,2,4]oxadiazolo[4,3-a]quinoxalin-1-one as a heme-site inhibitor of nitric oxide-sensitive guanylyl cyclase; Mol. Pharmacol. 50, 1 (1996)

Southam, E. et al.; The nitric oxide-cyclic GMP pathway and synaptic plasticity in the rat superior cervical ganglion; Br. J. Pharmacol. 119, 527 (1996)

Abi-Gerges, N. et al.; A comparative study of the effects of three guanylyl cyclase inhibitors on the L-type Ca2+ and muscarinic K+ currents in frog cardiac myocytes; Br. J. Pharmacol. 121, 1369 (1997)

Olson, L. J, et al.; Selective guanylyl cyclase inhibitor reverses nitric oxide-induced vasorelaxation; Hypertension 29, 254 (1997) Sobey C. G. & Faraci F. M.; Effects of a novel inhibitor of guanylyl cyclase on dilator responses of mouse cerebral arterioles; Stroke 28, 837 (1997)

Hwang, T. L. et al.; Comparison of two soluble guanylyl cyclase inhibitors, methylene blue and ODQ, on sodium nitroprusside-induced relaxation in guinea-pig trachea; Br. J. Pharmacol 125, 1158 (1998)

Motterlini, R et al.; Endothelial heme oxygenase-1 induction by hypoxia. Modulation by inducible nitric-oxide synthase and S-nitrosothiols; J. Biol. Chem. 275, 13613 (2000)

Sakuma, I. et al.; Identification of arginine as a precursor of endothelium-derived relaxing factor; PNAS 85, 8664 (1988)

Rees, D. D. et al.; A specific inhibitor of nitric oxide formation from L-arginine attenuates endothelium-dependent relaxation; Br. J. Pharmacol. 96, 418 (1989)

Garvey, E. P et al.; 1400W is a slow, tight binding, and highly selective inhibitor of inducible nitric-oxide synthase in vitro and in vivo; J. Biol. Chem. 272, 4959 (1997)

Thomsen, L. L. et al.; Selective inhibition of inducible nitric oxide synthase inhibits tumor growth in vivo: studies with 1400W, a novel inhibitor; Cancer Res. 57, 3300 (1997)

Laszlo F. & Whittle B. J. R.; Actions of isoform-selective and non-selective nitric oxide synthase inhibitors on endotoxin-induced vascular leakage in rat colon; Eur. J. Pharmacol. 334, 99 (1997)

Gumpricht, E. et al.; Nitric Oxide Ameliorates Hydrophobic Bile Acid-induced Apoptosis in Isolated Rat Hepatocytes by Non-mitochondrial Pathways; J. Biol. Chem. 277, 25823 (2002)

Moore, W. M. et al.; L-N-6-(1-iminoethyl)lysine: a selective inhibitor of inducible nitric oxide synthase; J. Med. Chem. 37, 3886 (1994)

Description of FIG. 1:

FIG. 1 shows a Dose response testing of the synthetic NO donor DEA NONOate on the stimulation of soluble guanylyl cyclase and detection of the subsequent cGMP production of guanylyl cyclase by employing the AlphaScreen cGMP competition assay outlined in Example 4.

The invention claimed is:

1. A method for measuring nitric oxide synthase activity, wherein the method comprises:
    (a) providing a solution comprising a nitric oxide synthase and a suitable substrate under conditions which allow synthesis of nitric oxide;
    (b) adding guanylyl cyclase and GTP under conditions which allow synthesis of cGMP; and
    (c) measuring cGMP, thereby measuring nitric oxide synthase activity.

2. The method according to claim 1, wherein the substrate is arginine.

3. The method according to claim 1, wherein cGMP is measured by an anti-cGMP specific antibody.

4. The method according to claim 1, wherein the nitric oxide synthase is i-NOS, e-NOS, or n-NOS.

5. A method for measuring nitric oxid synthase (NOS) activity in an high throughput (HTS) format wherein the method according to claim 1 is performed.

6. The method according to claim 5 wherein a plate having at least 96 wells is used.

7. The method according to claim 6 wherein a 384 well plate or a 1536 well plate is used.

8. The method according to claim 5 wherein a chip is used as a reaction and/or readout platform.

9. The method according to claim 1, wherein superoxide dismutase is added in step (b) together with guanylyl cyclase and GTP.

10. The method according to claim 1,wherein the method comprises: (a) providing a solution comprising a nitric oxide synthase, superoxide dismutase and a suitable substrate under conditions which allow synthesis of nitric oxide; (b) adding guanylyl cyclase and GTP under conditions which allow synthesis of cGMP; and (c) measuring cGMP, thereby measuring nitric oxide synthase activity.

11. The method according to claim 10 wherein the substrate is arginine.

12. The method according to claim 11 wherein cGMP is measured by an anti- cGMP specific antibody.

13. The method according to claim 11 wherein the nitric oxide synthase is i-NOS, e-NOS, or n-NOS.

14. A method for measuring nitric oxid synthase (NOS) activity in an high throughput (HTS) format wherein the method according to claim 10 is performed.

15. The method according to claim 14 wherein a plate having at least 96 wells-is used.

16. The method according to claim 15 wherein a 384 well plate or a 1536 well plate is used.

17. The method according to claim 14 wherein a chip is used as a reaction and/or readout platform.

* * * * *